(12) United States Patent
Gurcan et al.

(10) Patent No.: US 11,998,318 B2
(45) Date of Patent: Jun. 4, 2024

(54) SYSTEM AND METHOD OF USING VISUALLY-DESCRIPTIVE WORDS TO DIAGNOSE EAR PATHOLOGY

(71) Applicant: Ohio State Innovation Foundation, Columbus, OH (US)

(72) Inventors: Metin Gurcan, Winston-Salem, NC (US); Aaron Moberly, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 310 days.

(21) Appl. No.: 17/545,681

(22) Filed: Dec. 8, 2021

(65) Prior Publication Data

US 2022/0257150 A1   Aug. 18, 2022

Related U.S. Application Data

(60) Provisional application No. 63/148,763, filed on Feb. 12, 2021.

(51) Int. Cl.
  *A61B 5/12*  (2006.01)
  *A61B 5/00*  (2006.01)
  *G10L 15/08*  (2006.01)
  *G16H 50/20*  (2018.01)

(52) U.S. Cl.
  CPC ............ *A61B 5/126* (2013.01); *A61B 5/7264* (2013.01); *G10L 15/08* (2013.01); *G16H 50/20* (2018.01)

(58) Field of Classification Search
  CPC ..... A61B 5/126; A61B 5/7264; A61B 5/7267; A61B 1/227; A61B 1/00096; G10L 15/08; G16H 50/20; G16H 50/70; G06F 18/24; G06V 10/764
  See application file for complete search history.

(56) References Cited

U.S. PATENT DOCUMENTS

| | | | |
|---|---|---|---|
| 2002/0165466 A1 | 11/2002 | Givens et al. | |
| 2009/0271011 A1* | 10/2009 | Hyde | G16H 40/67 700/28 |
| 2010/0305963 A1 | 12/2010 | Firminger et al. | |
| 2013/0303941 A1 | 11/2013 | Porges et al. | |
| 2015/0065803 A1* | 3/2015 | Douglas | G06T 7/143 600/200 |
| 2016/0367188 A1 | 12/2016 | Malik et al. | |
| 2019/0216308 A1 | 7/2019 | Senaras et al. | |

OTHER PUBLICATIONS

International Search report and Written Opinion issued for Application No. PCT/US2021/062409, dated Jul. 1, 2022.
R. G. von Gioi, J. Jakubowicz, J.-M. Morel, and G. Randall, "LSD: A fast line segment detector with a false detection control," IEEE transactions on pattern analysis and machine intelligence, vol. 32, pp. 722-732, 2010.
H. Bay, T. Tuytelaars, and L. Van Gool, "Surf: Speeded up robust features," Computer vision—ECCV 2006, pp. 404-417, 2006.

(Continued)

*Primary Examiner* — Yogeshkumar Patel
(74) *Attorney, Agent, or Firm* — Meunier Carlin & Curfman LLC (57) ABSTRACT

Disclosed herein are systems and methods to detect a wide range of eardrum conditions by using visually-descriptive words of a tympanic membrane of a subject.

21 Claims, 7 Drawing Sheets

(56) References Cited

OTHER PUBLICATIONS

D. G. Lowe, "Distinctive image features from scale-invariant keypoints," International journal of computer vision, vol. 60, pp. 91-110, 2004.
E. Rublee, V. Rabaud, K. Konolige, and G. Bradski, "ORB: An efficient alternative to SIFT or SURF," in Computer Vision (ICCV), 2011 IEEE International Conference on, 2011, pp. 2564-2571.
M. A. Fischler and R. C. Bolles, "Random sample consensus: a paradigm for model fitting with applications to image analysis and automated cartography," Communications of the ACM, vol. 24, pp. 381-395, 1981.
H. Binol et al., "Decision fusion on image analysis and tympanometry to detect eardrum abnormalities," in Medical Imaging 2020: Computer-Aided Diagnosis, 2020, vol. 11314: International Society for Optics and Photonics, p. 113141M.
A. C. Moberly et al., "Digital otoscopy versus microscopy: How correct and confident are ear experts in their diagnoses?," Journal of telemedicine and telecare, vol. 24, No. 7, pp. 453-459, 2018.
D. Livingstone, A. S. Talai, J. Chau, and N. D. Forkert, "Building an Otoscopic screening prototype tool using deep learning," Journal of Otolaryngology—Head & Neck Surgery, vol. 48, No. 1, pp. 1-5, 2019.
R. M. Rosenfeld et al., "Clinical practice guideline: otitis media with effusion," Otolaryngology—Head and Neck Surgery, vol. 130, No. 5, pp. S95-S118, 2004.
A. Kuruvilla, N. Shaikh, A. Hoberman, and J. Kovačević, "Automated Diagnosis of Otitis Media: Vocabulary and Grammar," (in en), International Journal of Biomedical Imaging, pp. 1-15, 2013 2013, doi: 10.1155/2013/327515.
C. Senaras et al., "Autoscope: automated otoscopy image analysis to diagnose ear pathology and use of clinically motivated eardrum features," in Medical Imaging 2017: Computer-Aided Diagnosis, 2017, vol. 10134: International Society for Optics and Photonics, p. 101341X.
D. Cha, C. Pae, S.-B. Seong, J. Y. Choi, and H.-J. Park, "Automated diagnosis of ear disease using ensemble deep learning with a big otoendoscopy image database," EBioMedicine, vol. 45, pp. 606-614, 2019.
C. Senaras et al., "Detection of eardrum abnormalities using ensemble deep learning approaches," in Medical Imaging 2018: Computer-Aided Diagnosis, 2018, vol. 10575: International Society for Optics and Photonics, p. 105751A.
S. Camalan et al., "OtoMatch: Content-based eardrum image retrieval using deep learning," Plos one, vol. 15, No. 5, p. e0232776, 2020.
C. Gsaxner et al., "PET-train: Automatic ground truth generation from PET acquisitions for urinary bladder segmentation in CT images using deep learning," in 2018 11th Biomedical Engineering International Conference (BMEiCON), 2018: IEEE, pp. 1-5.
H. Binol et al., "SelectStitch: automated frame segmentation and stitching to create composite images from Otoscope video clips," Applied Sciences, vol. 10, No. 17, p. 5894, 2020.
Microsoft. (Dec. 20, 2018). Image Composite Editor (ICE) [Online]. Available: https://www.microsoft.com/en-us/research/product/computational-photography-applications/image-composite-editor/.
B. Jurish and K.-M. Würzner, "Word and Sentence Tokenization with Hidden Markov Models," J. Lang. Technol. Comput. Linguistics, vol. 28, No. 2, pp. 61-83, 2013.
C. Silva and B. Ribeiro, "The importance of stop word removal on recall values in text categorization," in Proceedings of the International Joint Conference on Neural Networks, 2003., 2003, vol. 3: IEEE, pp. 1661-1666.
M. Toman, R. Tesar, and K. Jezek, "Influence of word normalization on text classification," Proceedings of InSciT, vol. 4, pp. 354-358, 2006.
H. K. Kumar and B. Harish, "Classification of short text using various preprocessing techniques: An empirical evaluation," in Recent Findings in Intelligent Computing Techniques: Springer, 2018, pp. 19-30.
A. McCallum and K. Nigam, "A comparison of event models for naive Bayes text classification," in AAAI-98 workshop on learning for text categorization, 1998, vol. 752, No. 1: Citeseer, pp. 41-48.
J. Goldberger, G. E. Hinton, S. T. Roweis, and R. R. Salakhutdinov, "Neighbourhood components analysis," in Advances in neural information processing systems, 2005, pp. 513-520.
W. Yang, K. Wang, and W. Zuo, "Neighborhood Component Feature Selection for High-Dimensional Data," JCP, vol. 7, No. 1, pp. 161-168, 2012.

* cited by examiner

Create a database comprised of a plurality of tympanic membrane images and corresponding descriptions for each image, wherein each of the plurality of tympanic membrane images is associated with a TM diagnostic category
702

Analyze the database using artificial intelligence to determine a limited set of visually-descriptive words used to describe each TM diagnostic category
704

Receive a visual description of a TM of a subject from a healthcare provider
706

Make a diagnosis of the TM of the subject by analyzing the visual description provided by the healthcare provider
708

SYSTEM AND METHOD OF USING VISUALLY-DESCRIPTIVE WORDS TO DIAGNOSE EAR PATHOLOGY

CROSS REFERENCE TO RELATED APPLICATION

This application claims priority to and benefit of U.S. provisional patent application 63/148,763 filed Feb. 12, 2021, which is fully incorporated by reference and made a part hereof.

GOVERNMENT SUPPORT CLAUSE

This invention was made with government support under grant number R21 DC016972 awarded by the National Institutes of Health. The government has certain rights in the invention.

BACKGROUND

Ear infections, specifically acute infections of the middle ear (acute otitis media), are the most commonly treated childhood disease and account for approximately 20 million annual physician visits in the U.S. alone.

Ear diseases are one of the diseases that can easily be treated when diagnosed at the right time, and when appropriate treatment methods are applied. Otherwise, ear diseases may cause hearing loss or other complications. An otoscopic examination is one of the most basic and common tools used to examine the ear canal and eardrum (tympanic membrane, TM). However, an examination by an experienced and skillful physician may not always be possible. To help physicians who lack the same otoscopy experience, computer-aided diagnosis (CAD) systems may be useful. However, most CAD systems require obtaining and analyzing an image obtained from a subject undergoing examination. US PG-Patent Publication No. US 2019/0216308 A1 published Jul. 18, 2019, which is fully incorporated by reference, is an example of a content-based image retrieval (CBIR) system, which is also a good example of a CAD system designed to help physicians in making diagnostic decisions based on TM images.

However, image data can be large and difficult to transmit from remote sites to a location (and device) with processing power capable of performing the image analysis.

Therefore, systems and methods are desired that overcome challenges in the art, some of which are described above. In particular, there is a need for a timely and accurate method and system to make diagnostic decisions about TM conditions based on visually-descriptive words used to describe the condition of the TM to properly identify and classify any of a multitude of ear pathologies.

SUMMARY

Herein, creation of a database is described that utilizes a digital otoscopy video summarization and automated diagnostic label assignment model that benefits from the synergy of deep learning and natural language processing (NLP). Key visual features of TM diseases are obtained from short descriptive reports of TM images. Otoscopy records from a plurality of different TM diseases were obtained and composite images were generated for TM that exhibited visual indicators of the various disease, and normal TM. An ENT expert reviewed these composite images and wrote short reports describing the TM's visual landmarks and the disease for each ear. Based on NLP and a bag-of-words (BoW) model, a reduced set (e.g., five) most frequent words characterizing each TM diagnostic category were determined. These reduced sets of words and each set's corresponding TM condition (normal., TM disease 1, TM disease 2, . . . etc.) were then stored in a database. Once trained, the model can automatically create a reduced set of words characterizing the TM diagnostic category of additional images.

Once the model and database are created, visual descriptions of a subject's TM are then received from a healthcare provider and compared to the reduced sets of words. A diagnosis of the subject's TM condition is then made based on the best match between the visually-descriptive words received from the healthcare provider and the reduced sets of words associated with TM conditions, as stored in the database. In some instances, the disclosed systems, methods and computer program product comprise a telemedicine application in that the model can automatically make a diagnosis of the TM by analyzing its visual descriptions provided by a healthcare provider from a mobile device.

Additional advantages will be set forth in part in the description, which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and, together with the description, serve to explain the principles of the methods and systems:

FIGS. 5A-5D are example images of tympanic membrane (TM) conditions from the described dataset along with a normal TM for reference, where FIG. 5A is a normal TM.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application, including, but not limited to, steps in disclosed methods. Thus, if there are a variety of additional steps that can be performed, it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized, including hard disks, CD-ROMs, optical storage devices, or magnetic storage devices.

Embodiments of the methods and systems are described below with reference to block diagrams and flowchart illustrations of methods, systems, apparatuses, and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present methods and systems may be understood more readily by reference to the following detailed description of preferred embodiments and the Examples included therein and to the Figures and their previous and following description.

Figure 1:
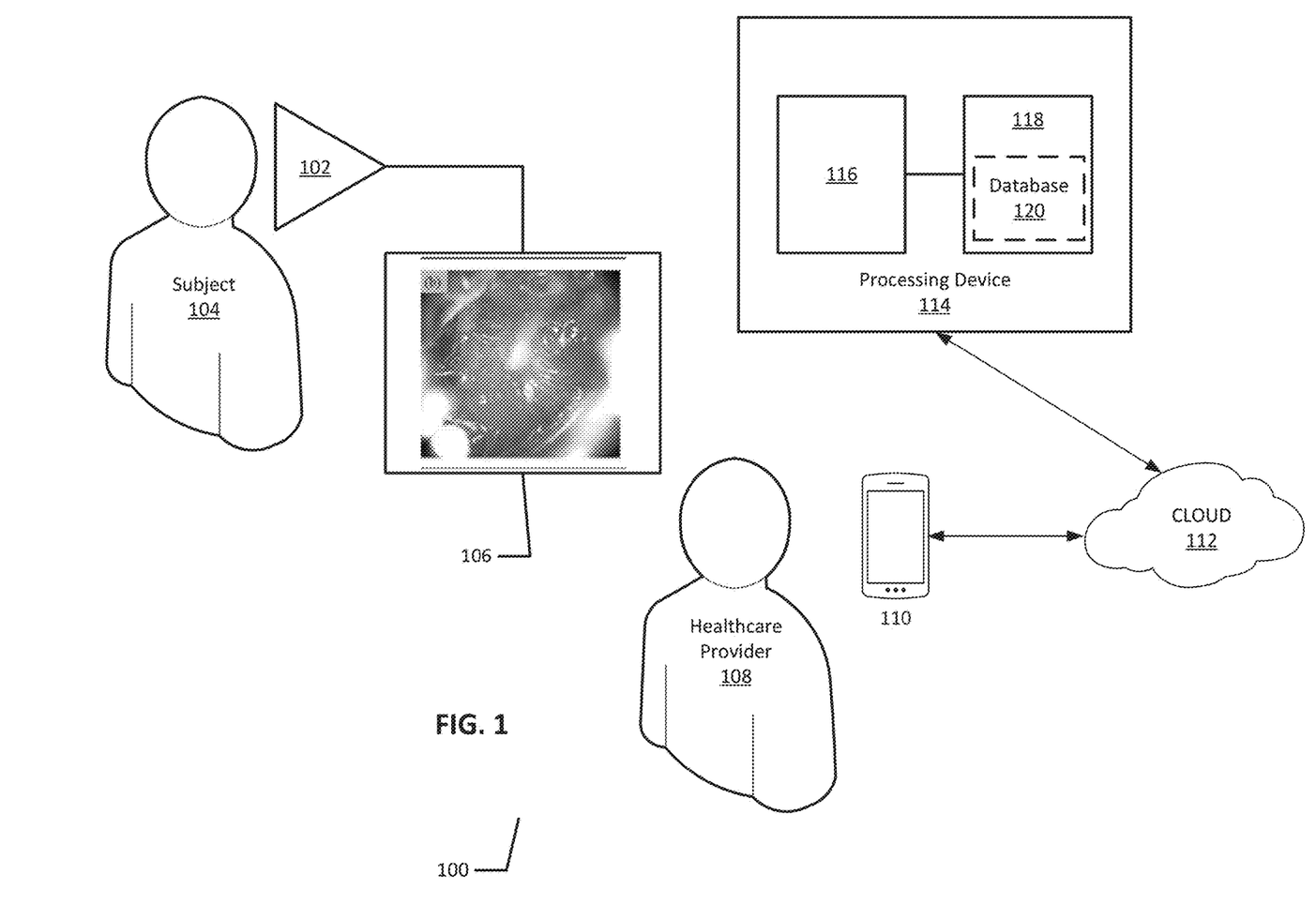
FIG. 1 illustrates an exemplary overview system for classifying ear pathologies from visual descriptors of a tympanic membrane of a subject.

FIG. 1 illustrates an exemplary overview system 100 for classifying ear pathologies from visual descriptors of a tympanic membrane of a subject 104. As shown in FIG. 1, one embodiment of the system 100 comprises an image capture mechanism 102. In one aspect, the image capture mechanism 102 can be a camera. More specifically, the image capture mechanism 102 may be a digital otoscope and/or a video otoscope. The image capture mechanism 102 can take still and/or video images of each ear. Generally, the image capture mechanism 102 is a digital camera, but can be an analog device equipped with or in communication with an appropriate analog/digital converter. The image capture mechanism 102 may also be a webcam, scanner, recorder, or any other device capable of capturing a still image or a video. In some instances, the system may comprise two image capture mechanisms 102 for capturing images of each ear either simultaneously or in sequence.

As shown in FIG. 1, the image capture mechanism 102 is in direct communication with a device configured to display images captured by the image capture device 102. For example, an otoscope or video otoscope may be connected to or integrated with a display 106. A healthcare provider 108 reviews the image or images on the display 106. The healthcare provider uses words to visually describe the one or more images of the tympanic membrane of the subject shown on the display 106. The visually-descriptive words may be spoken into or typed into a device 110, where they may be stored and are transmitted to a cloud computing architecture 112. The device 110 may comprise or be a part of a smart device such as a smart phone, tablet, laptop computer or any other fixed or mobile computing device. In some instances, the device 110 may be executing a specialized application for receiving the visually descriptive words (whether spoken or typed in) and transmitting them to the cloud computing architecture 112. The specialized application may have security features such that only the healthcare provider 108 and/or a designee of the healthcare provider 108 has access to the specialized application and/or the words used to describe the one or more images visually. Such security features may be those that are in compliance with government protocols for data security and privacy, such as HIPAA (in the United States). The cloud computing architecture 112 delivers the visually-descriptive words to a processing device 114. The processing device 114 may be a part of the cloud computing architecture 112 or it may be a processing device that is in communication with the cloud computing architecture 112. The visually descriptive words may be transmitted in real-time from the device 110 or may be stored in the device 110 and transmitted at a later time.

The processing device 114, in a basic configuration, can be comprised of a processor 116 and a memory 118. The processor 116 can execute computer-readable instructions that are stored in the memory 118. The processor 116 can further execute computer-readable instructions stored on the memory 118 to determine, using the received visually-descriptive words from the healthcare provider 108, and classify ear pathologies from the visually-descriptive words. Moreover, the processor 116 can execute computer-readable instructions to compare the visually descriptive words received from the healthcare provider to words in a database 120 residing in the memory 118 that have been selected by an artificial intelligence (AI) algorithm that are most-often used to make a diagnosis of a condition of the tympanic membrane of the ear from visually looking at images of tympanic membranes of ears with various conditions (e.g., Normal, Effusion, Retraction, Tympanosclerosis, etc.). The processor 116 then makes a match between the visually-descriptive words received from the healthcare provider and the closest descriptive words in the database that are used to describe a condition of the TM, such that a diagnosis of a condition of the ear can be made. The diagnosis is then transmitted back from the processing device 114 through the cloud computing architecture 112 to the device 110 of the healthcare provider 108, where the diagnosis of the ear (or ears) of the subject 104 is received by the healthcare provider 108.

In some instances, the visually descriptive words may be transmitted from the device 110 directly over a network (not shown in FIG. 1) to the processing device 114 for analysis, thereby omitting the cloud computing architecture 112. The network may comprise, for example, a wired (including fiber optic) network, wireless or a combination of wired and wireless) or a direct-connect cable (e.g., using a universal serial bus (USB) connection, IEEE 1394 "Firewire" connections, and the like). In other aspects, the visually descriptive words from the healthcare provider 108 may be recorded or stored on a memory device such that the visually descriptive words can be downloaded or transferred to the processing device 114 using, for example, a portable memory device and the like.

Figure 2:
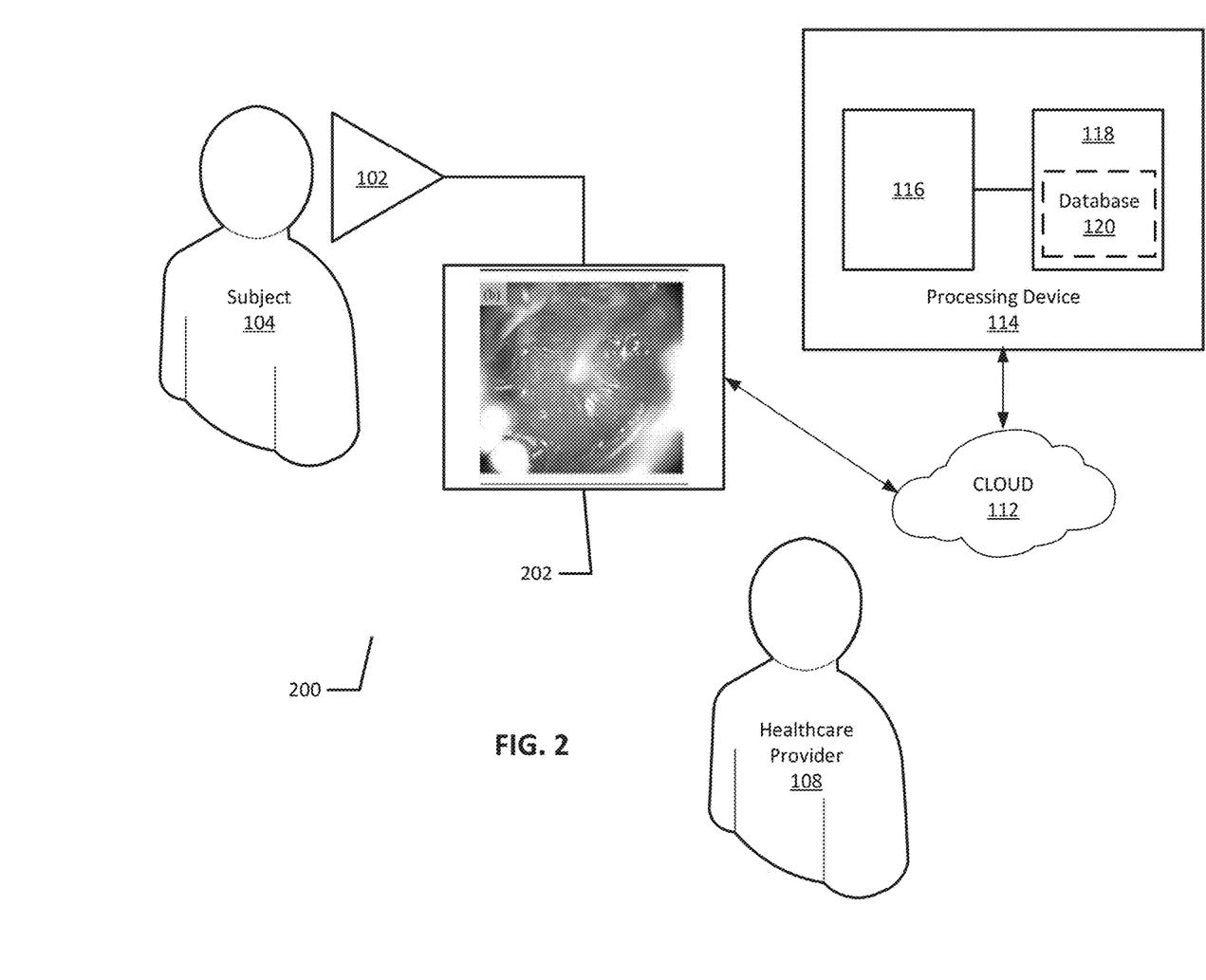
FIG. 2 illustrates an alternate exemplary overview system for classifying ear pathologies from visual descriptors of a tympanic membrane of a subject.

FIG. 2 illustrates an alternate exemplary overview system 200 for classifying ear pathologies from visual descriptors of a tympanic membrane of a subject. In the instance illustrated in FIG. 2, the image capture mechanism 102 captures an image of the TM of the subject 104, which is displayed on a display associated with device 202. Device 202 also includes a network interface mechanism that allows it to communicate with the cloud computing architecture 112 directly. Device 202 further includes I/O mechanisms such that the healthcare provider 108 can speak, type or otherwise enter visually-descriptive words about the TM of the subject 104 into the device 202 and transmit these visually-descriptive words to the cloud computing architecture 112 where they are compared, by the processing device 114, to the reduced sets of words in the database that are associated with corresponding TM conditions to make an automated diagnosis of the TM condition of the subject 104. The diagnosis then goes back to the device 202 through the cloud computing architecture 112, and provided to the healthcare provider 108. As with FIG. 1, in some instances, the cloud computing architecture 112 of FIG. 2 may be replaced with a direct network condition or, in some instances, the descriptive words from the healthcare provider may be stored and physically brought to the processing device for analysis. Device 202 may also be configured to execute an application, as described above, to display the images and transmit visually-descriptive words of the image as provided by the healthcare provider 108. As with the above, the application and/or device 202 may have data privacy and security protocols and may also transmit the visually-descriptive words in real-time, or store them for later transmission. In some instances, device 202 is a smart device such as a smart phone, tablet, laptop computer or any other fixed or mobile computing device.

Creating the Model

Figure 3:
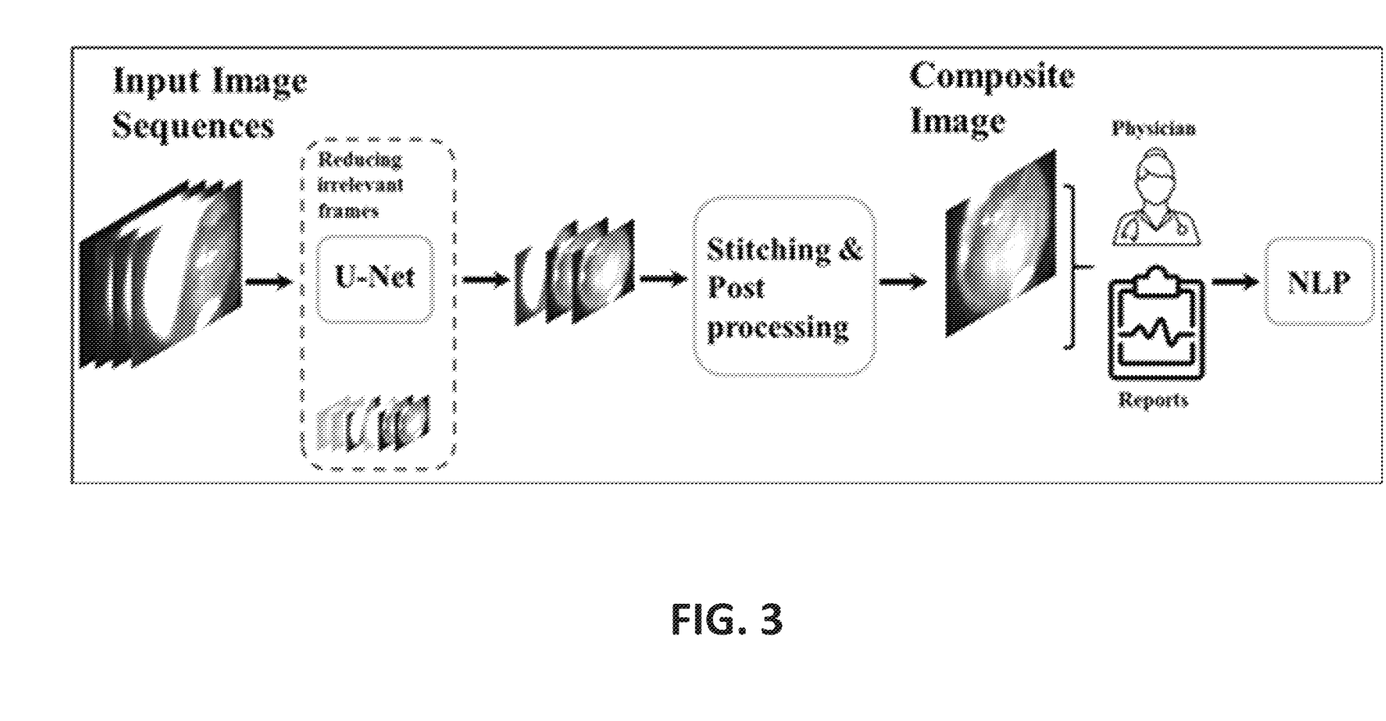
FIG. 3 illustrates a process for creating a model for composite image generation from otoscope images and/or video clips and creating reports by viewing the composite images.

FIG. 3 illustrates a process for creating a model for determining a diagnosis of a TM of a subject based upon visually-descriptive words used to describe a condition of the TM. The model begins with composite image generation from otoscope images and/or video clips and creating reports by viewing the composite images.

In the example of FIG. 3, images for creating the database were obtained from high-resolution digital adult and pediatric videos captured at ENT clinics and primary care settings at the Ohio State University (OSU) and Nationwide Children's Hospital (NCH) in Columbus, Ohio, USA. An Institutional Review Board (IRB) approved the data collection process. A high definition (HD) video otoscope (JEDMED Horus+ HD Video Otoscope, St. Louis, MO) was used to capture and record the video data. The dataset included 173 otoscope videos, including 86 instances of otitis media with effusion (this condition will be referred to as effusion for the rest of the paper), 35 instances of a retracted TM (referred to as retraction), and 52 instances of tympanosclerosis. After generating composite images, an ENT physician provided a diagnosis for each image, delineated the lesion on the TM images, and wrote a short descriptive report describing the corresponding TM abnormality's visual features. It is to be appreciated that other datasets may be used to create the composite images and corresponding reports.

Composite Image Generation

A U-Net based semantic segmentation method was utilized to determine the meaningful video frames from otoscopy videos, though other methods are contemplated to be within the scope of this disclosure. This process is described in greater detail with reference to FIG. 4, below. In this non-limiting example of the semantic segmentation task, the segmentation model was developed with 36 otoscope videos. The 764 frames were picked from those videos, and TM regions were manually identified and annotated by two ENT physicians.

The acquisition of adequate images can be a challenging task because of visual obstruction (e.g., wax, hair, etc.), poor illumination, a small field of view, black margins around the images, time/text stamps on the image, and the like. If the patient is a child, there may also be the problem of being able to capture a good still image while the patient is uncooperative. To solve these challenges, a short video (around 3-5 seconds) of each ear canal of the subject is captured. Then, software, executing the algorithm shown in FIG. 4, analyzes video frames of the eardrum and creates a new mosaicked image.

Figure 4:
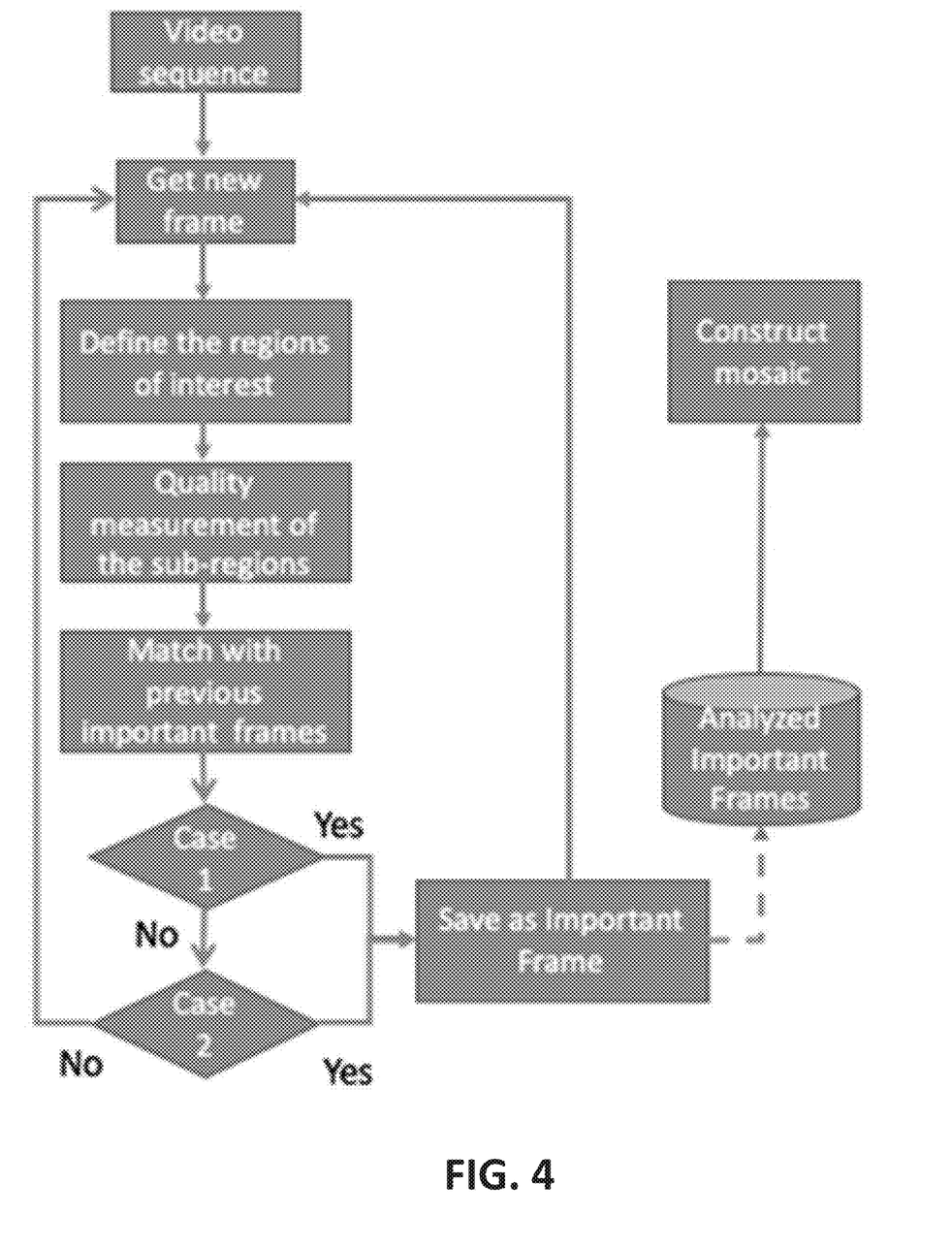
FIG. 4 illustrates a flow diagram for an exemplary composite image generation method where Case 1 occurs when a new frame includes new regions of interest that are not covered previously by another important frame, and Case 2 occurs if the region which is already covered by a previous important frame has a higher quality in this new frame.

For each new frame in the video sequence, the mosaic image creation algorithm as described in FIG. 4 determines the regions of interest which are free of obstruction (e.g., wax, hair, dark margins, text, etc.). Each of these regions is divided into subsections, and the image quality in each section is evaluated in terms of being in-focus, having adequate contrast and illumination. If the frame includes the part of the eardrum that is not included in the previous frames or includes an already included part of the eardrum but with higher quality (in terms of focus, contrast and illumination), then this frame is labeled as an "important frame" or otherwise identified. Finally, the method constructs the mosaic image by considering the regions of interest in all the "important frames" in the video sequence.

The frames may include different amounts of visual obstruction (e.g., wax, hair, glare, text, dark margins, etc.) and/or quality of illumination. As described herein, the method includes constructing composite obstruction-free images with excellent illumination. Therefore, the algorithm detects obstructions (wax, glare, hair, text, dark margins—see below) and out-of-focus regions during the composite image generation. To do that, the algorithm compares each new frame with the previous frames and updates the new image using the regions that are more in-focus and well-illuminated. To decide on in-focus and illumination quality, an image entropy is computed, and the frame with the highest entropy is selected.

Regarding wax detection, one of the typical characteristics of cerumen is its yellow color. Therefore, yellow regions are identified by using thresholding in CMYK color space. After these potential cerumen regions are detected as those regions with the highest "Y" values in the CMYK space, the mean and standard variation of the gradient magnitude of the intensities (i.e. "Y" values) of these cerumen regions are computed. These features are input to the FSG classifier to detect wax regions.

Glare is caused by the reflection of light from the otoscope on the surface of the tympanic membrane. Glare may be a problem for the calculation of some of the features (e.g., the mean color value of tympanic membrane). On the other hand, the cone of light, an important clinical diagnostic clue, can be inadvertently considered as glare by the glare detection algorithm and removed. In order to correctly extract the features, the disclosed method includes calculating the histogram of the intensity values and finds the peak corresponding to the highest intensity value in the histogram. That peak corresponds to the glare and cone of lights. To differentiate between the glare and cone of lights, area thresholding is applied (where glare(s) is larger than the cone of light(s)).

Hair detection includes detecting thin linear structures by using a line segment detector such as that described in R. G. von Gioi, J. Jakubowicz, J.-M. Morel, and G. Randall, "LSD: A fast line segment detector with a false detection control," IEEE transactions on pattern analysis and machine intelligence, vol. 32, pp. 722-732, 2010, which is incorporated by reference. Each hair strand is represented by two lines (both edges of the hair), approximately parallel to each other and the lines are close to each other. So, each approximately parallel line pair with a short distance is considered a hair candidate. The image texture is calculated between these parallel lines, and those with small textural variation are marked as hair.

In some instances, after the regions of interest are extracted, these regions are divided into 64×64 pixel blocks. For each block, the standard deviation, gray level co-occurrence matrix, contrast, and the mean intensity value are calculated. These values are weighted to calculate the tile quality. The weights may be determined manually or automatically.

To register two frames, points of interest are automatically extracted and the feature vectors for these points are matched. To extract points of interest, the performance of three state-of-the-art approaches is compared (see H. Bay, T. Tuytelaars, and L. Van Gool, "Surf: Speeded up robust features," Computer vision—ECCV 2006, pp. 404-417, 2006; D. G. Lowe, "Distinctive image features from scale-invariant keypoints," International journal of computer vision, vol. 60, pp. 91-110, 2004; and E. Rublee, V. Rabaud, K. Konolige, and G. Bradski, "ORB: An efficient alternative to SIFT or SURF," in Computer Vision (ICCV), 2011 IEEE International Conference on, 2011, pp. 2564-2571, each of which is fully incorporated by reference.). In order to identify the matched points, the approach computes the distance between all possible pairs of detected features in two frames. The approach estimates the initial Homograph matrix with Random Sample Consensus (RANSAC) (see M. A. Fischler and R. C. Bolles, "Random sample consensus: a paradigm for model fitting with applications to image analysis and automated cartography," Communications of the ACM, vol. 24, pp. 381-395, 1981, which is also incorporated by reference).

Each frame is identified as an "important frame" or not according to two criteria: (1) If the new frame includes new regions of interest which are not covered previously by another important frame; or (2), if the region which is already covered by a previous important frame has a higher quality in this new frame. A composite image can then be created by stitching. The disclosed method uses 'important frames" during the composite image construction. The algorithm selects the most suitable "important frames" for sub-parts of the eardrum and uses a multi-band blending (pyramid blending) method, which ensures smooth transitions between images despite illumination differences, while preserving high-frequency details.

Figure 5A:
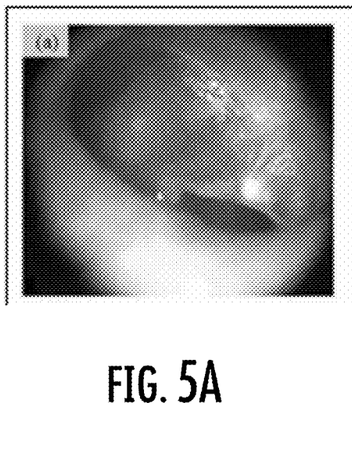
Figure 5B:
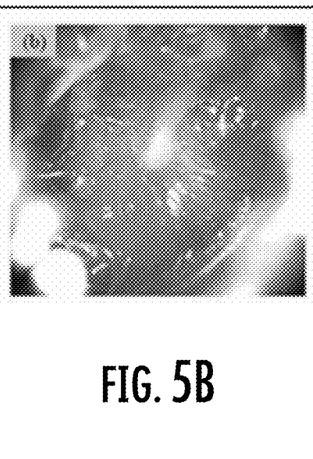
FIG. 5B is a TM with effusion.
Figure 5C:
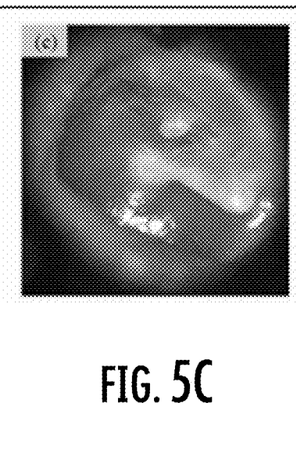
FIG. 5C is a TM with retraction.
Figure 5D:
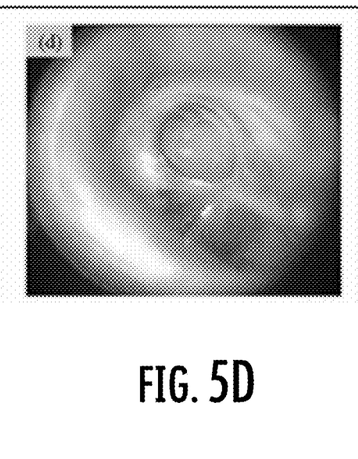
FIG. 5D is a TM with tympanosclerosis.

A freeware image stitching engine [12] was then used to create enhanced composite images by employing selected frames. FIGS. 5A-5D show examples of TM conditions from the described dataset along with a normal TM for reference, where FIG. 5A is a normal TM, FIG. 5B is a TM with effusion, FIG. 5C is a TM with retraction, and FIG. 5D is a TM with tympanosclerosis.

Text Analysis and Classification

Referring back to FIG. 3, several NLP tools were used in order to preprocess the TM reports of the ENT physician (i.e., expert) for analysis as follows: tokenization [13]; stop word removal [14]; word normalization [15]; and punctuation erasing [16].

A tokenized document is a document represented as a collection of words (also known as tokens). Words like "a," "and," and "to" (known as stop words) in English can add noise to data. Using a stop word removal functionality, these words were removed. Then, word normalization was used to reduce words to a root form (e.g., 'Connection'→'connect'). As the final preprocessing step, punctuation was removed from the text.

A bag-of-words (BoW) model [17] (also known as a term-frequency counter) was applied to obtain the number of times that words appear in each report, implying their frequency. To record the most important words in the BoW model for each diagnostic category, the five words with the highest word counts were specified for the training data, though more or fewer words may be used in other instances. For the multiclass classification of the preprocessed test report, a neighborhood components analysis (NCA) [18] was created using the BoW models of training data with the five most frequent words. NCA learns a linear transformation of data that maximizes k-nearest neighbor performance [19]. Moreover, generating a low-rank transformation, NCA provides dimensionality reduction, which extends the disclosure to high-dimensional feature space while integrating visual features with textual features.

Figure 6A:
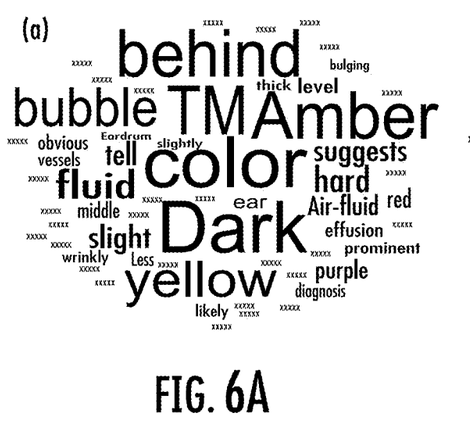
FIGS. 6A-6C illustrate examples of word clouds associated with certain TM conditions.
Figure 6B:
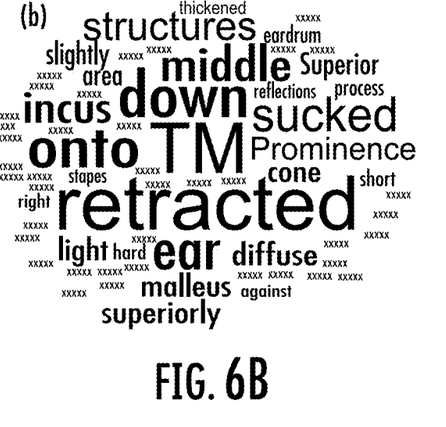
Figure 6C:
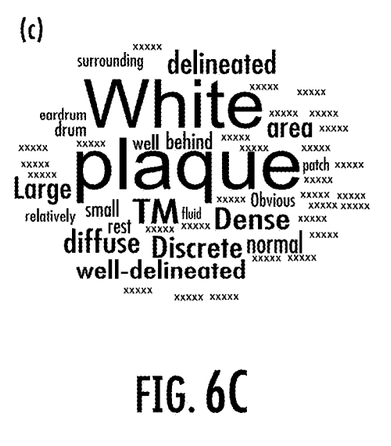

For each TM condition, word clouds were generated. See, for example, FIGS. 6A-6C. By analyzing the resulting word clouds, it can be seen that the keywords for effusion (FIG. 6A) were mainly indicating the color features such as "amber" and "dark." For retraction (FIG. 6B), the keywords were "retracted" and "sucked," and for tympanosclerosis (FIG. 6C), a lesion was mostly described with the words "white" and "plaque." Word clouds can be generated in this manner for any number of TM conditions, including the "normal" condition. Once trained, the model can automatically create a reduced set of words characterizing the TM diagnostic category of additional images.

Figure 7:
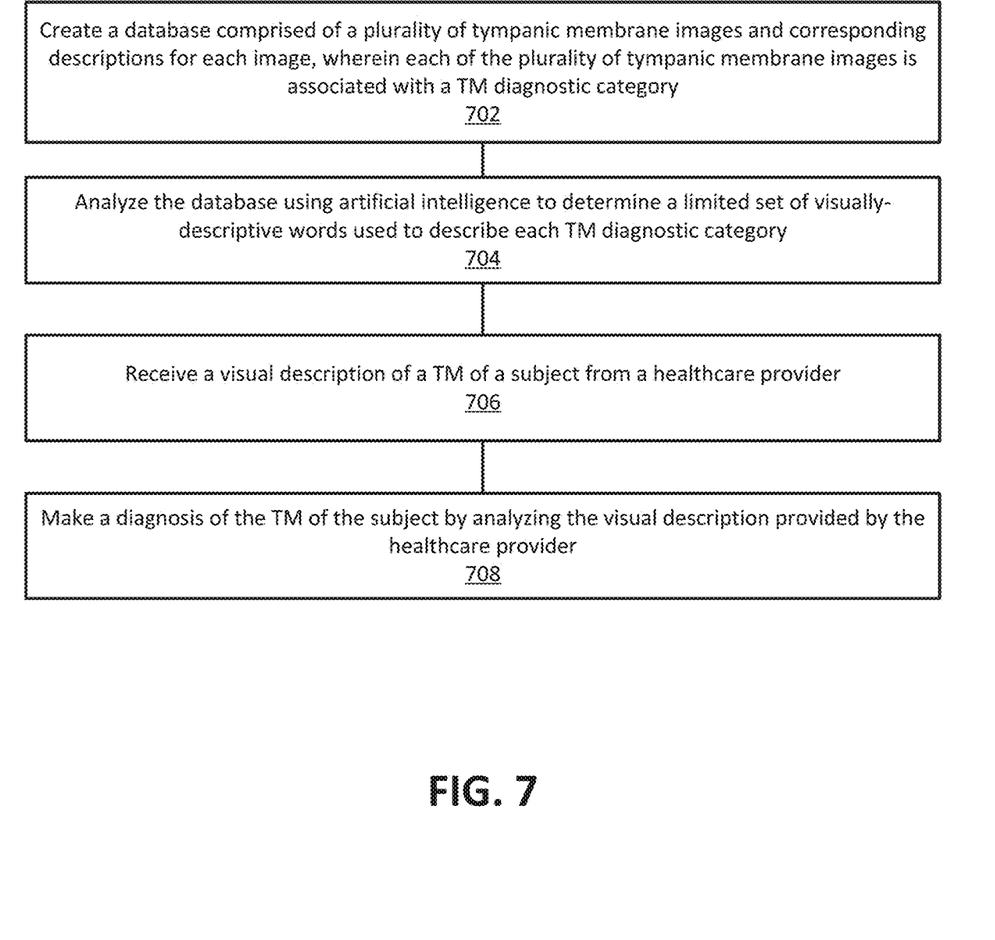
FIG. 7 is a flowchart that illustrates an exemplary method of classifying ear pathologies from visually descriptive words describing a subject's TM.

Once a database of TM conditions and the associated word clouds of each condition is created, it can be used to make determinations about the TM condition of a subject when a healthcare provider visually describes the TM of the subject. FIG. 7 is a flowchart that illustrates an exemplary method of classifying ear pathologies from visually descriptive words describing a subject's TM. Steps 702 and 704 describe the process of creating a database of word clouds and associated TM conditions, as described above. At 706, one or more words that provide a visual description of the TM of a subject are received from a healthcare provider. These words may be received in a variety of ways, as described herein. For example, they may be expressed by the voice of the healthcare provider, in real-time or recorded, or they may be provided in written format (e.g., text). The one or more words of the visual description are received electronically, and at 708 they are compared, using a processing device executing computer-executable instructions, to the word clouds associated with various TM conditions in the database. The closest fit is found between the one or more visual description words and a word cloud. The TM condition that corresponds with the selected word cloud is then provided as the diagnosis of the TM of the subject.

The system has been described above as comprised of units. One skilled in the art will appreciate that this is a functional description and that the respective functions can be performed by software, hardware, or a combination of software and hardware. A unit can be software, hardware, or a combination of software and hardware. The units can comprise software for making a determination of a diagnosis of a TM condition based upon words visually describing the TM of a subject. In one exemplary aspect, the units can comprise a computing device that comprises a processor 821 as illustrated in FIG. 8 and described below.

Figure 8:
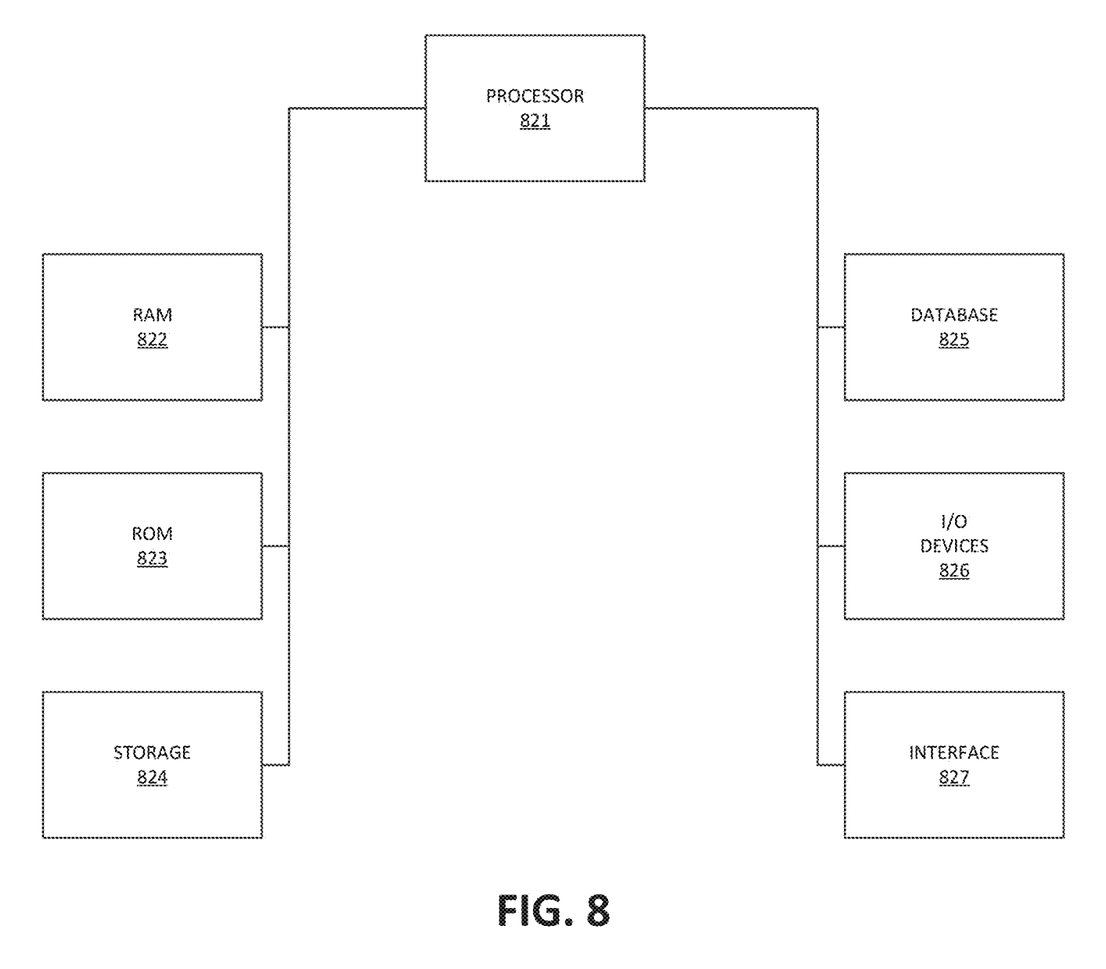
FIG. 8 illustrates an exemplary computer that can be used for classifying tympanic membrane pathologies using the right and left eardrum otoscopy images of a subject.

FIG. 8 illustrates an exemplary computer that can be used for classifying tympanic membrane pathologies from images. As used herein, "computer" may include a plurality of computers. The computers may include one or more hardware components such as, for example, a processor 821, a random access memory (RAM) module 822, a read-only memory (ROM) module 823, a storage 824, a database 825, one or more input/output (I/O) devices 826, and an interface 827. Alternatively and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 824 may include a software partition associated with one or more other hardware components. It is understood that the components listed above are exemplary only and not intended to be limiting.

Processor 821 may include one or more processors, each configured to execute instructions and process data to perform one or more functions associated with a computer for classifying pathologies of an eardrum based upon one or more images of the eardrum. Processor 821 may be communicatively coupled to RAM 822, ROM 823, storage 824, database 825, I/O devices 826, and interface 827. Processor 821 may be configured to execute sequences of computer program instructions to perform various processes. The computer program instructions may be loaded into RAM 822 for execution by processor 821.

RAM 822 and ROM 823 may each include one or more devices for storing information associated with the operation of processor 821. For example, ROM 823 may include a memory device configured to access and store information associated with the computer, including information for identifying, initializing, and monitoring the operation of one or more components and subsystems. RAM 822 may include a memory device for storing data associated with one or more operations of processor 821. For example, ROM 823 may load instructions into RAM 822 for execution by processor 821.

Storage 824 may include any type of mass storage device configured to store information that processor 821 may need to perform processes consistent with the disclosed embodiments. For example, storage 824 may include one or more magnetic and/or optical disk devices, such as hard drives, CD-ROMs, DVD-ROMs, or any other type of mass media device.

Database 825 may include one or more software and/or hardware components that cooperate to store, organize, sort, filter, and/or arrange data used by the computer and/or processor 821. For example, database 825 may store a plurality of word clouds, and a TM condition associated with each word cloud, along with computer-executable instructions for receiving one or more words that visually describe a TM of a subject; comparing the one or more visually descriptive words to each of the plurality of word clouds, determining the closest fit between the one or more visually descriptive words and one of the word clouds; and diagnosing a condition of the TM of the subject based on the TM condition associated with the selected word cloud. It is contemplated that database 825 may store additional and/or different information than that listed above.

I/O devices 826 may include one or more components configured to communicate information with a user associated with computer. For example, I/O devices may include a console with an integrated keyboard and mouse to allow a user to maintain a database of digital images, results of the analysis of the digital images, metrics, and the like. I/O devices 826 may also include a display including a graphical user interface (GUI) for outputting information on a monitor. I/O devices 826 may also include peripheral devices such as, for example, a printer for printing information associated with the computer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 827 may include one or more components configured to transmit and receive data via a communication network, such as the Internet, a local area network, a workstation peer-to-peer network, a direct link network, a wireless network, or any other suitable communication platform. For example, interface 827 may include one or more modulators, demodulators, multiplexers, demultiplexers, network communication devices, wireless devices, antennas, modems, and any other type of device configured to enable data communication via a communication network.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process.

Experimental Setup

Three global evaluation measures, i.e., sensitivity, specificity, and F1-Score, were used to evaluate the proposed model's performance.

Sensitivity is computed as:

$$\text{Sensitivity} = \frac{TP}{TP + FN} \quad (1)$$

Specificity as:

$$\text{Specificity} = \frac{TN}{TN + FP} \quad (2)$$

and F1-Score as:

$$F1 - \text{Score} = \frac{2 \times TP}{(2 \times TP + FN + FP)} \quad (3)$$

where TP denotes the number of true positives, TN the number of true negatives, FP the number of false positives, and FN the number of false negatives. A leave-one-patient-out cross-validation scheme was applied to validate our model.

Results and Discussion

Word clouds were created for eardrum conditions of effusion, retraction, and tympanosclerosis, as described herein.

The classifier's confusion matrix, which is based on text classification from bag-of-words using top-5 words for each TM category, is presented in Table 1.

TABLE 1

|  | Predicted label | Effusion | Retraction | Tympanosclerosis |
|---|---|---|---|---|
| Actual label | Effusion | 86 | 0 | 0 |
|  | Retraction | 8 | 26 | 1 |
|  | Tympanosclerosis | 6 | 0 | 46 |

The NCA Predictor Confusion Matrix

From 86 instances of descriptions labeled as effusion, the model predicted all of them correctly. On the other hand, 26 instances were successfully predicted as retraction, with nine misclassifications; 46 instances were predicted as tympanosclerosis with six misclassifications. Table 2 lists the sensitivity, specificity, and F1-Score of the proposed classification model based on these values.

TABLE 2

| Diagnostic Category | Sensitivity | Specificity | F1-Score |
|---|---|---|---|
| Effusion | 100.0 | 83.9 | 92.5 |
| Retraction | 74.3 | 100.0 | 85.3 |
| Tympanosclerosis | 88.5 | 99.2 | 92.9 |
| Overall | 87.6 | 94.4 | 90.2 |

Performance Results Obtained by the Proposed Model in Terms of Sensitivity, Specificity, and F1-Score in Percentage As shown in Table 2, the experimental results showed that an embodiment of the disclosed model performed effectively (overall F1-Score is 90.2%) in the task of diagnostic label prediction of otoscopy records using short descriptive reports. It is worth noticing that our model uses the top-5 words in any disease category instead of all the words. Our aim in determining the top-5 words was to obtain the "key" words for each disease and explore the model's efficiency with these keywords.

It was also observed that the model predicted almost all of the misclassified retraction and tympanosclerosis instances as effusion. Effusion is one of the hardest TM conditions to identify and distinguish from others. In the misclassified instances, the ENT physician mainly described findings as suspicious for, but not clearly, effusion. For example, the true label was determined as retraction by the ENT physician instead of effusion, whereas he wrote some minor visual evidence of effusion, but he evaluated these pieces of evidence as subtle. Hence, our model estimated these instances as effusion.

Conclusions

There is a growing interest in the analysis of TM imagery. While most of these studies focus on image analysis and disease classification, it is important to develop other data sources that could be useful in better diagnosis and treatment. One such source could be physician observations and notes. This study's main contributions are to analyze the TM reports, describe different types of TM abnormalities generated by reviewing composite images of raw otoscopy videos and predict the label of the test instance from these reports using NLP and machine learning. In one example, we extracted the five most frequent words from each category using NLP techniques and created a classifier based on these five words from training data. By following a leave-one-patient-out cross-validation method, the exemplary model achieved 92.5%, 85.3%, and 92.9% F1-Score for effusion, retraction, and tympanosclerosis, respectively. Thus, it is shown that using textual features can provide satisfactory information for the computerized diagnosis of TM videos and images.

REFERENCES

Throughout this application, various publications may be referenced. The disclosures of these publications in their entireties are hereby fully incorporated by reference into this application in order to more fully describe the state of the art to which the methods and systems pertain. The below publications are each fully incorporated by reference and made a part hereof:

[1] H. Binol et al., "Decision fusion on image analysis and tympanometry to detect eardrum abnormalities," in *Medical Imaging* 2020: *Computer-Aided Diagnosis*, 2020, vol. 11314: International Society for Optics and Photonics, p. 113141M.
[2] A. C. Moberly et al., "Digital otoscopy versus microscopy: How correct and confident are ear experts in their diagnoses?," *Journal of telemedicine and telecare*, vol. 24, no. 7, pp. 453-459, 2018.
[3] D. Livingstone, A. S. Talai, J. Chau, and N. D. Forkert, "Building an Otoscopic screening prototype tool using deep learning," *Journal of Otolaryngology—Head & Neck Surgery*, vol. 48, no. 1, pp. 1-5, 2019.
[4] R. M. Rosenfeld et al., "Clinical practice guideline: otitis media with effusion," *Otolaryngology—Head and Neck Surgery*, vol. 130, no. 5, pp. S95-S118, 2004.
[5] A. Kuruvilla, N. Shaikh, A. Hoberman, and J. Kovačević, "Automated diagnosis of otitis media: vocabulary and grammar," *Journal of Biomedical Imaging, vol.* 2013, p. 27, 2013.
[6] C. Senaras et al., "Autoscope: automated otoscopy image analysis to diagnose ear pathology and use of clinically motivated eardrum features," in *Medical Imaging* 2017: *Computer-Aided Diagnosis*, 2017, vol. 10134: International Society for Optics and Photonics, p. 101341X.
[7] D. Cha, C. Pae, S. -B. Seong, J. Y. Choi, and H. -J. Park, "Automated diagnosis of ear disease using ensemble deep learning with a big otoendoscopy image database," *EBioMedicine*, vol. 45, pp. 606-614, 2019.
[8] C. Senaras et al., "Detection of eardrum abnormalities using ensemble deep learning approaches," in *Medical Imaging* 2018: *Computer-Aided Diagnosis*, 2018, vol. 10575: International Society for Optics and Photonics, p. 105751A.
[9] S. Camalan et al., "OtoMatch: Content-based eardrum image retrieval using deep learning," *Plos one*, vol. 15, no. 5, p. e0232776, 2020.
[10] C. Gsaxner et al., "PET-train: Automatic ground truth generation from PET acquisitions for urinary bladder segmentation in CT images using deep learning," in 2018 11*th Biomedical Engineering International Conference (BMEiCON)*, 2018: IEEE, pp. 1-5.
[11] H. Binol et al., "SelectStitch: Automated Frame Segmentation and Stitching to Create Composite Images from Otoscope Video Clips," *Applied Sciences*, vol. 10, no. 17, p. 5894, 2020.
[12] Microsoft. (Dec. 20, 2018). *Image Composite Editor (ICE)* [Online]. Available: https://www.microsoft.com/en-us/research/product/computational-photography-applications/image-composite-editor/.
[13] B. Jurish and K. -M. Würzner, "Word and Sentence Tokenization with Hidden Markov Models," *J. Lang. Technol. Comput. Linguistics*, vol. 28, no. 2, pp. 61-83, 2013.
[14] C. Silva and B. Ribeiro, "The importance of stop word removal on recall values in text categorization," in *Proceedings of the International Joint Conference on Neural Networks*, 2003, 2003, vol. 3: IEEE, pp. 1661-1666.
[15] M. Toman, R. Tesar, and K. Jezek, "Influence of word normalization on text classification," *Proceedings of InSciT*, vol. 4, pp. 354-358, 2006.
[16] H. K. Kumar and B. Harish, "Classification of short text using various preprocessing techniques: An empirical evaluation," in *Recent Findings in Intelligent Computing Techniques*: Springer, 2018, pp. 19-30.
[17] A. McCallum and K. Nigam, "A comparison of event models for naive Bayes text classification," in *AAAI*-98 *workshop on learning for text categorization*, 1998, vol. 752, no. 1: Citeseer, pp. 41-48.
[18] J. Goldberger, G. E. Hinton, S. T. Roweis, and R. R. Salakhutdinov, "Neighbourhood components analysis," in *Advances in neural information processing systems*, 2005, pp. 513-520.
[19] W. Yang, K. Wang, and W. Zuo, "Neighborhood Component Feature Selection for High-Dimensional Data," *JCP*, vol. 7, no. 1, pp. 161-168, 2012.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method of classifying tympanic membrane pathologies from descriptive words, comprising:
 receiving one or more descriptive words describing a condition of a tympanic membrane of a subject; and
 determining, by a computing device, using a model comprised of a plurality of tympanic membrane conditions and corresponding word clouds, wherein each word cloud is comprised of words most frequently associated with each one of the plurality of tympanic membrane conditions as determined by an artificial intelligence algorithm, a diagnosis of the tympanic membrane of the subject based on the received one or more descriptive words describing the condition of the tympanic membrane of the subject, wherein the model is developed by obtaining a plurality of images of tympanic membranes having the plurality of tympanic membrane conditions, forming a composite image of a tympanic membrane for each of the plurality of tympanic membrane conditions, having a specialist provide a descriptive report of each composite image and its corresponding tympanic membrane condition; and analyzing using the artificial intelligence algorithm each specialist descriptive report to determine the word cloud of words most frequently associated with the corresponding tympanic membrane image, and wherein one or more natural language processing (NLP) tools were used to preprocess each specialist descriptive report, said NLP tools comprising one or more of tokenization, stop word removal, word normalization, and punctuation erasing.

2. The method of claim 1, wherein the one or more descriptive words are received electronically as a voice of a healthcare provider, or wherein the one or more descriptive words are received electronically as text, and wherein the one or more descriptive words are received in real-time, or wherein the one or more descriptive words are recorded and received later in time.

3. The method of claim 1, wherein a bag-of-words (BoW) model (also known as a term-frequency counter) was applied to each preprocessed specialist descriptive report to obtain a number of times that particular words appear in each report, implying their frequency.

4. The method of claim 1, wherein once the model is trained, the model can automatically create a word cloud characterizing additional tympanic membrane images.

5. The method of claim 1, wherein determining, the diagnosis of the tympanic membrane of the subject based on the received one or more descriptive words describing the condition of the tympanic membrane of the subject comprises comparing the received one or more descriptive words describing the condition of the tympanic membrane to the word clouds using neighborhood components analysis (NCA), where NCA learns a linear transformation of data that maximizes k-nearest neighbor performance.

6. The method of claim 1, wherein the model comprises a database that associates each of the plurality of tympanic membrane conditions with its corresponding word cloud.

7. The method of claim 1, wherein the diagnosis of the tympanic membrane of the subject is one of normal, effusion, retraction, or tympanosclerosis.

8. A system for classifying tympanic membrane pathologies from descriptive words, comprising:
 a device configured to view a tympanic membrane of a subject; and
 a processor in communication with a memory, wherein the memory contains computer-executable instructions that when executed by the processor cause the processor to:
  receive one or more descriptive words describing a condition of the tympanic membrane of a subject; and
  determine, using a model comprised of a plurality of tympanic membrane conditions and corresponding word clouds, wherein each word cloud is comprised of words most frequently associated with each one of the plurality of tympanic membrane conditions as determined by an artificial intelligence algorithm, a diagnosis of the tympanic membrane of the subject based on the received one or more descriptive words describing the condition of the tympanic membrane of the subject, wherein the model is developed by obtaining a plurality of images of tympanic membranes having the plurality of tympanic membrane conditions, forming a composite image of a tympanic membrane for each of the plurality of tympanic membrane conditions, having a specialist provide a descriptive report of each composite image and its corresponding tympanic membrane condition; and analyzing using the artificial intelligence algorithm each specialist descriptive report to determine the word cloud of words most frequently associated with the corresponding tympanic membrane image, and wherein one or more natural language processing (NLP) tools were used to preprocess each specialist descriptive report, said NLP tools comprising one or more of tokenization, stop word removal, word normalization, and punctuation erasing.

9. The system of claim 8, wherein the one or more descriptive words are received electronically as a voice of a healthcare provider or wherein the one or more descriptive words are received electronically as text, and wherein the one or more descriptive words are received in real-time, or wherein the one or more descriptive words are recorded and received later in time.

10. The system of claim 8, wherein a bag-of-words (BoW) model (also known as a term-frequency counter) was applied to each preprocessed specialist descriptive report to obtain a number of times that particular words appear in each report, implying their frequency.

11. The system of claim 8, wherein once the model is trained, the model can automatically create a word cloud characterizing additional tympanic membrane images.

12. The system of claim 8, wherein the processor executing computer-executable instructions that cause the processor to determine the diagnosis of the tympanic membrane of the subject based on the received one or more descriptive words describing the condition of the tympanic membrane of the subject comprises the processor executing computer-readable instructions that cause the processor to compare the received one or more descriptive words describing the condition of the tympanic membrane to the word clouds using neighborhood components analysis (NCA), where NCA learns a linear transformation of data that maximizes k-nearest neighbor performance.

13. The system of claim 8, wherein the model comprises a database stored in the memory that associates each of the plurality of tympanic membrane conditions with its corresponding word cloud.

14. The system of claim 8, wherein the diagnosis of the tympanic membrane of the subject is one of normal, effusion, retraction, or tympanosclerosis.

15. A non-transitory computer-program product comprising computer executable code sections stored on a computer-readable medium, said computer executable code sections for performing a method of classifying tympanic membrane pathologies from descriptive words, comprising:
 receiving one or more descriptive words describing a condition of a tympanic membrane of a subject; and
 determining, using a model comprised of a plurality of tympanic membrane conditions and corresponding word clouds, wherein each word cloud is comprised of words most frequently associated with each one of the plurality of tympanic membrane conditions as determined by an artificial intelligence algorithm, a diagnosis of the tympanic membrane of the subject based on the received one or more descriptive words describing the condition of the tympanic membrane of the subject, wherein the model is developed by obtaining a plurality of images of tympanic membranes having the plurality of tympanic membrane conditions, forming a composite image of a tympanic membrane for each of the plurality of tympanic membrane conditions, having a specialist provide a descriptive report of each composite image and its corresponding tympanic membrane condition; and analyzing using the artificial intelligence algorithm each specialist descriptive report to determine the word cloud of words most frequently associated with the corresponding tympanic membrane image, and wherein one or more natural language processing (NLP) tools were used to preprocess each specialist descriptive report, said NLP tools comprising one or more of tokenization, stop word removal, word normalization, and punctuation erasing.

16. The computer-program product of claim 15, wherein the one or more descriptive words are received electronically as a voice of a healthcare provider or wherein the one or more descriptive words are received electronically as text, and wherein the one or more descriptive words are received in real-time, or wherein the one or more descriptive words are recorded and received later in time.

17. The computer-program product of claim 15, wherein a bag-of-words (BoW) model (also known as a term-frequency counter) was applied to each preprocessed specialist descriptive report to obtain a number of times that particular words appear in each report, implying their frequency.

18. The computer-program product of claim 15, wherein once the model is trained, the model can automatically create a word cloud characterizing additional tympanic membrane images.

19. The computer-program product of claim 15, wherein determining, the diagnosis of the tympanic membrane of the subject based on the received one or more descriptive words describing the condition of the tympanic membrane of the subject comprises comparing the received one or more descriptive words describing the condition of the tympanic membrane to the word clouds using neighborhood components analysis (NCA), where NCA learns a linear transformation of data that maximizes k-nearest neighbor performance.

20. The computer-program product of claim 15, wherein the model comprises a database that associates each of the plurality of tympanic membrane conditions with its corresponding word cloud.

21. The computer-program product of claim 15, wherein the diagnosis of the tympanic membrane of the subject is one of normal, effusion, retraction, or tympanosclerosis.

* * * * *